United States Patent [19]

Holt et al.

[11] Patent Number: 4,970,204
[45] Date of Patent: Nov. 13, 1990

[54] 3-SUBSTITUTED NITRO-STEROID DERIVATIVES AS 5-α-REDUCTASE INHIBITORS

[75] Inventors: Dennis A. Holt, Mohnton; Mark A. Levy, Wayne; Brian W. Metcalf, Radnor, all of Pa.

[73] Assignee: SmithKline Beecham Corporation, Philadelphia, Pa.

[21] Appl. No.: 397,615

[22] Filed: Aug. 23, 1989

[51] Int. Cl.$^5$ ...................... A61K 31/56; A61K 31/58
[52] U.S. Cl. .................................. 514/169; 514/176; 514/177; 552/521
[58] Field of Search ................ 514/170, 176, 177, 169

[56] References Cited

U.S. PATENT DOCUMENTS

| 4,191,759 | 3/1980 | Johnston et al. | 514/177 |
| 4,317,817 | 3/1982 | Blohm et al. | 514/150 |
| 4,361,578 | 11/1982 | Alig et al. | 514/462 |
| 4,377,584 | 3/1983 | Rasmusson et al. | 514/284 |
| 4,814,324 | 3/1989 | Borris et al. | 514/26 |

FOREIGN PATENT DOCUMENTS 0289327 11/1988 European Pat. Off. .

OTHER PUBLICATIONS

Journal of Medical Chemistry, 11(2), pp. 285-287 (1968).
Chemical Abstracts vol. 68: 87452z (1968).
Chemical Abstracts vol. 105: 153386s (1986).
Hsia and Voight, J. Invest. Dermat. 62: 224-227 (1974).
Robaire et al., J. Steroid Biochem. 8: 307-310 (1977).
Blohm et al., Biochem, Biophys. Res. Comm. 95: 273-280 (1980).
Liang et al., J. Steriod Biochem. 19, 385-390 (1983).
Petrow et al., Steroids 38: 121-140 (1981).
Brooks et al., Steroids 47: 1-19 (Jan. 1986).

Primary Examiner—Douglas W. Robinson
Assistant Examiner—Kevin E. Weddington
Attorney, Agent, or Firm—Wayne J. Dustman; Stuart R. Suter; Edward T. Lentz

[57] ABSTRACT

Invented are 3-nitro- substituted steroidal synthetic compounds, pharmaceutical compositions containing the compounds, and methods of using these compounds to inhibit steroid 5-α-reductase including using these compounds to reduce prostate size. Also invented are intermediates used in preparing these compounds.

15 Claims, No Drawings ial

3-SUBSTITUTED NITRO-STEROID DERIVATIVES AS 5-α-REDUCTASE INHIBITORS

FIELD OF THE INVENTION

The present invention relates to certain novel analogues of steroidal synthetic compounds having unsaturated bonds in the 3-nitro-substituted A ring, pharmaceutical compositions containing these compounds, and methods for using these compounds to inhibit mammalian steroid 5-α-reductase.

DESCRIPTION OF RELATED ART

The class of steroidal hormones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective production control results in excessive androgen hormone production. For example, acne vulgaris, seborrhea, female hirsutism, and benign prostatic hypertrophy are correlated with elevated androgen levels. Additionally, the incidence of male pattern baldness has been associated with high androgen levels.

Testosterone is the principal androgen secreted by the testes and is the primary androgenic steroid in the plasma of males. It now is known that 5-α-reduced androgens are active hormones in some tissues such as the prostate and sebaceous gland. Circulating testosterone thus serves as a prohormone for dihydrotestosterone (DHT), its 5-α-reduced analogue in these tissues but not in others such as muscle and testis. Steroid 5-α-reductase is a NADPH-dependent enzyme that converts testosterone to DHT. The importance of this enzyme in male development was dramatically underscored by discovery of a genetic steroid 5-α-reductase deficiency in male pseudohermaphrodites. Imperato-McGinley, J., et. al., (1979), *J. Steroid Biochem.* 11 637–648.

Recognition of the importance of elevated DHT levels in many disease states has stimulated many efforts to synthesize inhibitors of this enzyme. Several known steroid 5-α-reductase inhibitors have been disclosed.

The first inhibitor described was the 17β-carboxylic acid steroid by Hsia and Voight in 1973. *J. Invest. Dermat.* 224–227. A sectosteroid was to be described and also has found utility as an affinity label for 5-α-reductase. Robaire, B., et. al., (1977), *J. Steroid Biochem.* 8:307–310. A diazoketone steroid has been reported as a potent, time-dependent inhibitor of steroid 5-α-reductase. Blohm, T. R., et. al. (1980), *Biochem. Bioohvs. Res. Comm.* 95: 273–208; U.S. Pat. No. 4,317,817, Mar. 2, 1982. A group of 4-aza steroid inhibitors of steroid 5-α-reductase were described in U.S. Pat. No. 4,377,584 which issued Mar. 22, 1983, and in Liang, T., et. al., (1983), *J. Steroid Biochem.* 19, 385–390. A 6-methylene steroid also has been shown to be a time-dependent inactivator of steroid 5-α-reductase. Petrow, V., et. al. (1981), *Steroids* 38:121–140.

Other steroid 5-α-reductase inhibitors also have been described. U.S. Pat. No. 4,361,578 which issued June 2, 1986, describes a class of homosteroid enzyme inhibitors. U.S. Pat. No. 4,191,759 discloses amides of 17β-carboxy-4-androsten-3-one that are active as steroid 5-α-reductase inhibitors. Japanese Pat. Nos. J60146855-A and J60116657-A disclose various aniline derivatives having numerous activities including 5-α-reductase inhibiting activity. Japanese Pat. No. I60142941-A discloses phenylsubstituted ketones having 5-α-reductase inhibiting activity and European Pat. No. EP173516-A discloses various phenylsubstituted amides having similar activity Shiseido referenced terpene derivatives that are active inhibitors of steroid 5-α-reductase. Japanese Pat. No. J59053417-A.

SUMMARY OF THE INVENTION

The present invention resides in the discovery that 5-α-reductase is inhibited by certain 3-nitro-substituted unsaturated A-ring analogues of synthetic steroidal compounds. The compounds are potent enzyme inhibitors.

Presently preferred compounds of the invention and compounds used in the invented pharmaceutical compositions and the invented methods include:

17β-N,N-Diisopropylcarboxamide-3-nitro-5-α-androst-3-ene,

17β-N-t-Butylcarboxamide-3-nitro-5-α-androst-3-ene, and

17β-N,N-Diisopropylcarboxamide-3-nitro-5-α-androst-2-ene.

In a further aspect of the invention there are provided novel intermediates and novel processes useful in preparing the presently invented 5-α-reductase inhibiting compounds.

The invention also is a method for inhibiting 5-α-reductase activity in mammals, including humans, that comprises administering internally to a subject an effective amount of a presently invented 5-α-reductase inhibiting compound. Included in the present invention are pharmaceutical compositions comprising a pharmaceutical carrier and compounds useful in the methods of the invention.

DETAILED DESCRIPTION OF THE INVENTION

The presently invented compounds that inhibit 5-α-reductase have the following Formula (I):

in which:

The A ring has one double bond where indicated by the broken lines;

R is (1) α-hydrogen, α-hydroxyl, or α-acetoxy and/or $$-W-\overset{O}{\underset{\|}{C}}-R^2 \qquad (a)$$

where W is a bond or $C_{1-12}$alkylidene and $R_2$ is
(i) $C_{1-8}$alkyl,
(ii) $C_{1-8}$alkoxy, or
(iii) $NR^3R^4$, where $R^3$ and $R^4$ are each independently selected from hydrogen, $C_{1-8}$alkyl, $C_{3-}$ 6cycloalkyl, phenyl; or R³ and R⁴ taken together with the nitrogen to which they are attached represent a 5-6 membered saturated ring comprising up to one other heteroatom selected from oxygen and nitrogen, (2) =CH—W—CO—R² or =CH—W—OR⁵, where W is a bond or $C_{1-12}$alkylidene, R² has the same meaning as above, and R⁵ is
  (i) phenyl $C_{1-6}$alkylcarbonyl,
  (ii) $C_{5-10}$cycloalkylcarbonyl,
  (iii) benzoyl,
  (iv) $C_{1-8}$alkoxycarbonyl,
  (v) aminocarbonyl, or $C_{1-8}$alkyl substituted aminocarbonyl,
  (vi) hydrogen,
  (vii) $C_{1-8}$alkyl, or
  (viii) $C_{1-20}$alkylcarbonyl;

(3) α-hydrogen and NHCOR⁶ where R⁶ is $C_{1-12}$alkyl or NR³R⁴ where R³ and R⁴ have the same meaning as above, or (4) keto;

or a pharmaceutically acceptable salt thereof.

As used herein unless otherwise specified, $C_{1-n}$alkyl and $C_{1-n}$alk means a straight or branched hydrocarbon chain having 1 to n carbons and alk means a straight or branched hydrocarbon chain having 1 to 12 carbons.

Preferred among the presently invented compounds are those having Formula (II):

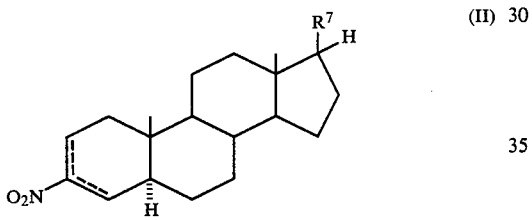

(II)

in which:

The A-ring has one double bond where indicated by the broken lines;

R⁷ is
(a) CONR⁸R⁹ wherein R⁸ and R⁹ independently are H or $C_{1-8}$alkyl, or
(b) CH(CH₃)CH₂OR¹⁰ where R¹⁰ is H or $C_{1-6}$alkyl;

or a pharmaceutically acceptable salt thereof.

Particularly preferred are Formula (II) compounds in which the A-ring has a $C_3$-$C_4$ double bond.

Compounds of Formula (I) are included in the pharmaceutical compositions of the invention and used in the methods of the invention.

As used above and throughout the remainder of the specification and claims, the carbons of the steroid nucleus are numbered and the rings are lettered in standard nomenclature as follows:

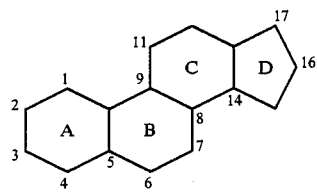

Schemes I and II show formation of Formula (I) compounds which are Formula (I) compounds in which R is replaced by R¹ which is R or moieties which can be converted to those of R by known chemical reactions such as described in J. Fried and J. Edwards, *Organic Reactions in Steroid Chemistry*, Pub: Van Nostrand Reinhold Company (1972). As demonstrated in the following Examples, reactions to convert R¹ to R are performed on products of synthetic pathway of Schemes I and II or, where appropriate or preferable, on certain intermediates in this synthetic pathway.

SCHEME I

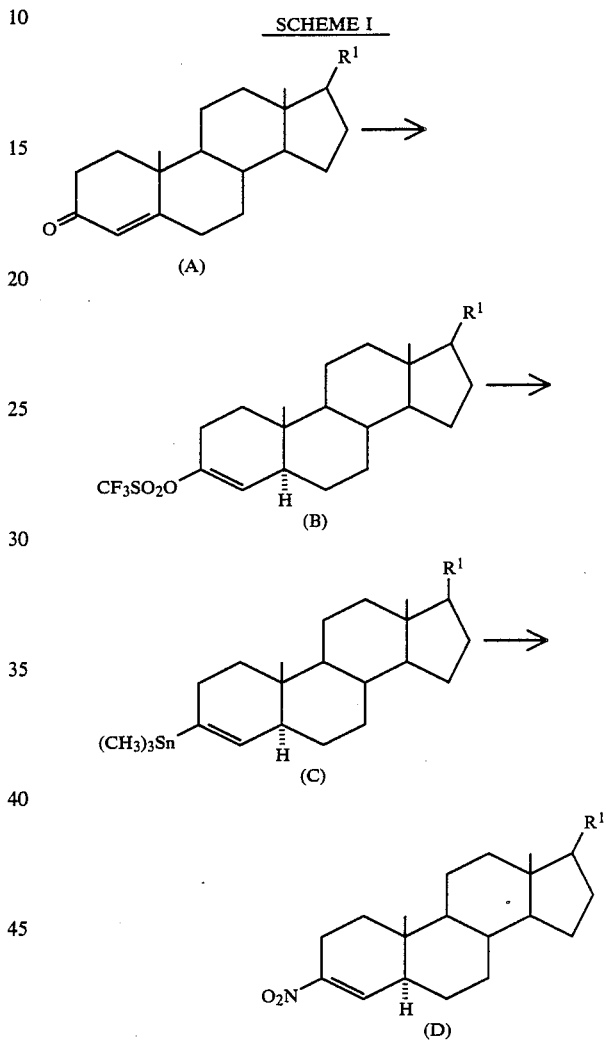

Scheme I depicts formation of Formula (I) compounds which have one double bond in the A-ring. The starting 4-ene-3-one compounds (A) are known and readily available and are synthesized from available precursors using known procedures as described in European patent application 88303878.8. Formula (A) compounds are reduced in a suitable organic proton donor such as t-butanol, or preferably aniline, in an appropriate organic solvent, preferably tetrahydrofuran (THF) when added to a reducing metal amine, preferably a lithium/ammonia (Li/NH₃) solution, to form a reaction mixture. This reaction mixture is stirred at −100° C. to −30° C., preferably at −78° C., quenched with a lithium scavenger such as dibromomethane, bromobenzene, or preferably isoprene, and evaporated to form a residue. Formula (B) compounds then are prepared by reacting the residue dissolved in a suitable organic solvent, preferably THF, with an N-aryltrihaloalkyl-sulfonimide, preferably N-phenyltrifluoromethylsulfonimide at a temperature of −20° C. to 20° C.

Formula (C) compounds, which are vinyl stannane derivatives of steroids, are prepared by a modification of reported procedures (J. Organic Chem., (1986), 51, 277–279). The formula (C) compounds are prepared from the vinyl triflates compounds (B). Compounds (B) are dissolved in a suitable solvent, preferably THF, and treated with hexamethyldistannane, lithium chloride, lithium carbonate and phosphine palladium catalyst, preferably tetrakis(triphenylphosphine) palladium (0). This reaction mixture is degassed and stirred under an argon atmosphere for 4 hours at 60° C. The reaction mixture was quenched with ammonium chloride to provide the vinyl stannanes compounds of formula (C) compounds. Formula (D) compounds are prepared from formula (C) compounds by a reported procedures (Tetra. Letters, (1980), 1113–1116) by stirring tetranitromethane with formula (C) compounds in refluxing carbon tetrachloride for 18 hours.

SCHEME II

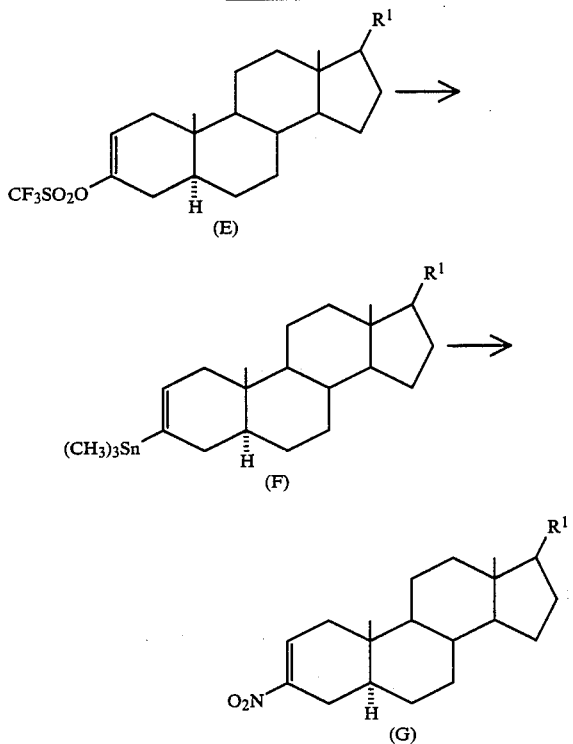

Scheme II illustrates synthesis of Formula (I) compounds in which a $C_2$-$C_3$ double bond is substituted with a nitro group at the 3-position. Compounds (E) are obtained by known procedures from 3-one precursors as described in European patent appl. 88303878 8. The methods shown in Scheme II were used to convert the triflates compounds (E) to the vinyl stannanes compounds (F). Compounds (G) are prepared from compounds (F) in a manner analogous to the procedures used in Scheme I.

Pharmaceutically acceptable acid addition salts of compounds of the invention containing a basic group are formed where appropriate with strong or moderately strong organic or inorganic acids in the presence of a basic amine by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the acid addition salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Because Formula (I) compounds inhibit steroid 5-α-reductase activity, they have therapeutic utility in treating diseases and conditions wherein decreases in DHT activity produce the desired therapeutic effect. Such diseases and conditions include acne vulgaris, seborrhea, female hirsutism, prostate diseases such as benign prostatic hypertrophy, and male pattern baldness.

The potency of multiple compounds of the invention was tested for potency in inhibiting human steroid 5-α-reductase using tissue from hyperplastic human prostates. In determining potency in inhibiting the human enzyme, the following procedure was employed Frozen human prostates were thawed and minced into small pieces (5mm$^3$). The tissue was homogenized in 3 to 5 volumes of 20 mM potassium phosphate, pH 6.5, buffer containing 0.33 M sucrose, 1 mM dithiothreitol, and 50 μM NADPH with a Brinkmann Polytron (Sybron Corporation, Westbury, N.Y.). The solution was subjected to sonication for 3 to 5 minutes with a Sonifier (Branson Sonic Power Co.) followed by hand homogenization in a glass-to-glass Dounce homogenizer (Kontes Glass Company, Vineland, N.J.).

Prostatic particles were obtained by differential centrifugation at 600 or 1000×g for 20 minutes and 140,000 ×g for 60 minutes at 4° C. The pellet obtained from the 140,000×g centrifugation was washed with 5 to 10 tissue volumes of the buffer described above and recentrifuged at 40,000×g. The resulting pellet was suspended in 20 mM potassium phosphate buffer, pH 6.5, containing 20% glycerol, 1 mM dithiothreitol, and 50 μM NADPH. The suspended particulate solution was stored at −80° C.

A constant amount of [$^{14}$C]-testosterone (52 to 55 mCi/mmol, New England Nuclear, Boston, Mass.) in ethanol and varying amounts of the potential inhibitor in ethanol were deposited in test tubes and concentrated to dryness in a SAVANT Speed Vac. To each tube was added buffer, 20 ml of 10 mM NADPH and an aliquot of prostatic particulate solution to a final volume of 0.5 ml of 50 mM sodium citrate, pH 5.0. After incubating the solution at 37° C. for 20 to 30 minutes the reaction was quenched by the addition of 4 ml ethyl acetate and 0.25 μmol each of testosterone, dihydrotestosterone, androstanediol, and androstanedione as carriers. The organic layer was removed to a second test tube and evaporated to dryness in vacuo. The residue was dissolved in 20 to 30 μl chloroform, spotted on an individual lane of a 20 ×20 cm prechanneled silica gel TLC plate (Si 250F-PA, Baker Chemical) and developed twice with acetone:chloroform (1:9). The radiochemical content in the bands of the substrate and the products was determined with a BIOSCAN Imaging Scanner (Bioscan, Inc., Washington, D.C.). The percent of recovered radiolabel converted to product was calculated, from which enzyme activity was determined. All incubations were conducted such that no more than 12% of the substrate (testosterone) was consumed.

The experimentally obtained data was computer fitted to a linear function by plotting the reciprocal of the enzyme activity (1/velocity) against the variable inhibitor concentration (Dixon, M. (1953), *Biochem J.* 55, 170). Assuming that the steroidal inhibitor is a competitive inhibitor against testosterone, a value for the inhibition constant ($K_i$) can be calculated from equation 1:

$$K_i = (B/A)/(S/K_m + 1) \qquad \text{Equation 1}$$

where B is the intercept on the 1/velocity axis, A is the slope of the line, S is the concentration of substrate (testosterone) used in the experiment, and $K_m$ is the Michaelis-Menton constant of the substrate (testosterone) determined in a separate experiment to be 4.5 μM. The compound 17β-N,N-diisopropylcarboxamide-3-nitro-5-α-androst-3-ene, when tested in the above manner, exhibited a $K_i$ of 50 nM with the human enzyme, while the 2-ene analogue exhibited a $K_i$ of 250 nM.

The compounds of Formula (I) are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension. The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the present compounds of Formula (I) in a pharmaceutical dosage unit as described above will be an efficacious, nontoxic quantity selected from the range of 0.1–1000 mg/kg of active compound, preferably 1–100 mg/kg. The selected dose is administered to a human patient in need of steroid 5-α-reductase inhibition from 1–6 times daily, topically, orally, rectally, by injection, or continuously by infusion. Oral dosage units for human administration preferably contain from 1 to 500 mg of active compound. Parenteral administration, which uses lower dosages is preferred. Oral administration, at higher dosages, however, also can be used when safe and convenient for the patient.

The invented methods of inhibiting steroid 5-α-reductase activity in mammals, including humans, comprises administering internally to a subject an effective steroid 5-α-reductase inhibiting amount of a compound of Formula (I). The invented methods of reducing prostate size which include methods of reducing the rate at which prostate size increases comprise administering internally to a subject an effective amount of a Formula (I) compound.

The following examples illustrate preparation of Formula (I) compounds and pharmaceutical compositions containing these compounds. The examples are not intended to limit the scope of the invention as defined hereinabove and as claimed below.

EXAMPLE 1

17β-N,N-Diisopropylcarboxamide-3-nitro-5-α-androst-3-ene

(i)

17β-N,N-Diisopropylcarboxamide-3-trifluoromethylsulfonate-5-α-androst-3-ene

Ammonia (500 mL) was double distilled into a flask equipped with a dry ice condenser and an argon bubbler. Lithium wire (1 g) was dissolved in the ammonia. Freshly distilled aniline (1.85 g) was added followed by a solution of 17β-N,N-diisopropylcarboxamide-3-oxoandrost-4-ene (European patent appl. 88303878.8) (10 g) in dry THF (200 mL) that was added dropwise. Then the reaction was stirred at −78° C. to −33° C. for 2 hours, and then quenched with isoprene until the blue color was discharged. The volatiles were slowly evaporated and then the residue was pumped at 0.5 mmHG for 1 hour. The oily residue was dissolved in dry THF (200 mL), cooled to 0° C. and a solution of N-phenyltrifluoromethylsulfonimide (25 g) in THF (100 mL) was added. This mixture was stirred at 0° C. for 18 hours, concentrated to dryness and the residue was chromatographed on silica gel with 10% ethyl acetate in hexane to afford 17β-N,N-diisopropylcarboxamide-3-trifluoromethylsulfonate-5-α-androst-3-ene (8.6 g, 64%).

(ii)

17β-N,N-diisopropylcarboxamide-3-trimethylstannyl-5-α-androst-3-ene

A mixture of 17β-N,N-diisopropylcarboxamide-3-trifluoromethylsulfonate-5-α-androst-3-ene (1.1 g), hexamethylstannane (1.15 g), lithium chloride (1 g), lithium carbonate (0.25 g), tetrakis (triphenylphosphine) palladium (0) (0.2 g), and THF (25 mL) was degassed by three freeze-thaw cycles under vacuum, and then the mixture was heated under argon at 60° C. for 4 hours according to the procedure described in *J. Organic Chemistry*, 51, 277–279 (1986). The cooled reaction mixture was partitioned between ethyl acetate and saturated aqueous ammonium chloride, and the dried, concentrated organic phase was chromatographed over silica gel with 70% ethyl acetate and 1% triethylamine in hexanes to give 17β-N,N-diisopropylcarboxamide-3-trimethylstannyl-5-α-androst-3-ene (800 mg, 70%).

(iii)

17β-N,N-Diisopropylcarboxamide-3-nitro-5-α-androst-3-ene

A suspension of 17β-N,N-diisopropylcarboxamide-3-trimethylstannyl-5-α-androst-3-ene (30 mg, 0.11 mmole) in carbon tetrachloride (2 mL) was treated with tetranitromethane (20 mg) according to the procedure described (*Tetra. Letters*, 1980, 1113–1116). The mixture was refluxed for 18 hours, cooled, concentrated and chromatographed (silica gel, 10% ethyl acetate in hexane) to afford 17β-N,N-diisopropylcarboxamide-3-nitro-5-α-androst-3-ene (9 mg); m.p. 194°–197° C.

EXAMPLE 2

17β-N-t-Butylcarboxamide-3-nitro-5-α-androst-3-ene

The title compound is prepared according to Example 1 (ii-iii) by using 17β-N-t-butylcarboxamide-3-trifluoromethylsulfonate-5-α-androst-3-ene (European patent appl. 88303878.8) in place of 17β-N,N-diisopropylcarboxamide-3-trifluoromethyl-sulfonate-androst-3-ene.

EXAMPLE 3

17β-N,N-Diisopropylcarboxamide-3-nitro-5-α-androst2-ene

17β-N,N-diisopropylcarboxamide-3-nitro-5-α-androst-2-ene, (m.p. 133°–135° C.) is prepared according to Example 1 (ii-iii) by using 17β-N,N-diisopropylcarboxamide-3-trifluoromethylsulfonate-5-α-androst-2-ene (European patent appl. 88303878.8) in place of 17β-N,N-diisopropylcarboxamide-3-trifluoromethyl-sulfonate-5-α-androst-3-ene.

EXAMPLE 4

An oral dosage form for administering Formula (I) compounds is produced by screening, mixing, and filling into hard gelatin capsules the ingredients in the proportions shown in Table I, below.

TABLE I

| Ingredients | Amounts |
| --- | --- |
| 17β-N,N-Diisopropylcarboxamide-3-nitro-5-α-androst-3-ene | 50 mg |
| magnesium stearate | 5 mg |
| lactose | 75 mg |

EXAMPLE 5

The sucrose, calcium sulfate dihydrate and Formula (I) compound shown in Table II below, are mixed and granulated in the proportions shown with a 10% gelatin solution. The wet granules are screened, dried, mixed with the starch, talc and stearic acid, screened and compressed into a tablet.

TABLE II

| Ingredients | Amounts |
| --- | --- |
| 17β-N,N-Diisopropylcarboxamide-3-nitro-5-α-androst-3-ene | 100 mg |
| calcium sulfate dihydrate | 150 mg |
| sucrose | 20 mg |
| starch | 10 mg |
| talc | 5 mg |
| stearic acid | 3 mg |

EXAMPLE 6

17β-N,N-Diisopropylcarboxamide-3-nitro-5-α-androst-3-ene (1.0 g) is dissolved in 20 g of soybean oil and emulsified by mixing with 1.2 g of egg phospholipid and enough water to bring the final volume to 100 ml. The formed interlipid formulation is suitable for intravenous administration.

While the preferred embodiments of the invention are illustrated by the above, it is to be understood that the invention is not limited to the precise instructions herein disclosed and that the right to all modifications coming within the scope of the following claims is reserved.

What is claimed is:

1. A Compound represented by the formula:

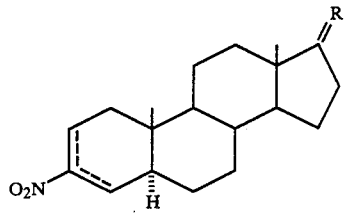

in which:
the A-ring has a $C_2$-$C_3$ or $C_3$-$C_4$ double bond where indicated by the broken lines;
R is
(1) α-hydrogen, α-hydroxyl, or α-acetoxy and/or

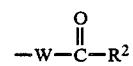

where W is a bond or $C_{1-12}$alkylidene and $R_2$ is
(i) $C_{1-8}$alkyl,
(ii) $C_{1-8}$alkoxy, or independently selected from hydrogen, $C_{1-8}$alkyl, $C_{3-6}$cycloalkyl, phenyl; or $R^3$ and $R^4$ taken together with the nitrogen to which they are attached represent a 5–6 membered saturated ring comprising up to one other heteroatom selected from oxygen and nitrogen,
(2) =CH—W—CO—$R^2$ or =CH—W—O$R^5$, where W is a bond or $C_{1-12}$alkylidene, $R^2$ has the same meaning as above, and $R^5$ is
(i) phenyl $C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$alkyl substituted aminocarbonyl,
(vi) hydrogen,
(vii) $C_{1-8}$alkyl, or
(viii) $C_{1-20}$alkylcarbonyl;
(3) α-hydrogen and NHCO$R^6$ where $R^6$ is $C_{1-12}$alkyl or N$R^3R^4$ where $R^3$ and $R^4$ have the same meaning as above, or
(4) keto;
or a pharmaceutically acceptable salt thereof.

2. A compound of claim 1 having the following formula:

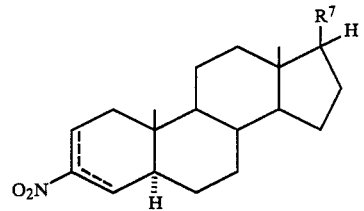

in which:
The A-ring has one double bond where indicated by the broken lines;
$R^7$ is
(a) CON$R^8R^9$ wherein $R^8$ and $R^9$ independently are H or $C_{1-8}$alkyl, or
(b) CH(CH$_3$)CH$_2$O$R^{10}$ where $R^{10}$ is H or $C_{1-6}$alkyl, or a pharmaceutically acceptable salt thereof.

3. A compound of claim 2 wherein the A-ring has a $C_3$-$C_4$ double bond.

4. A compound of claim 1 that is 17β-N,N-diisopropylcarboxamide-3-nitro-5-α-androst-3-ene.

5. A compound of claim 1 that is 17β-N-t-butylcarboxamide-3-nitro-5-α-androst-3-ene.

6. A compound of claim 1 that is 17β-N,N-diisopropylcarboxamide-3-nitro-5-α-androst-2-ene.

7. A pharmaceutical composition comprising a suitable pharmaceutical carrier and a therapeutically effective amount of compound of claim 1.

8. A composition of claim 7 wherein the compound is 17β-N,N-diisopropylcarboxamide-3-nitro-5-α-androst-3-ene.

9. A composition of claim 7 wherein the compound is 17β-N-t-butylcarboxamide-3-nitro-5-α-androst-3-ene.

10. A composition of claim 7 wherein the compound is 17β-N,N-diisopropylcarboxamide-3-nitro-5-α-androst-2-ene.

11. A method of inhibiting steroid 5-α-reductase activity in a mammal, in need thereof, that comprises administering internally to the subject a therapeutically effective amount of a compound of claim 1.

12. A method of reducing prostate size in a mammal in need thereof that comprises administering to a subject a therapeutically effective amount of a compound of claim 1.

13. A method of claim 11 wherein the compound is 17β-N,N-diisopropylcarboxamide-3-nitro-5-α-androst-3-ene.

14. A method of claim 11 wherein the compound is 17β-N-t-butylcarboxamide-3-nitro-5-α-androst-3-ene.

15. A method of claim 11 wherein the compound is 17β-N,N-diisopropylcarboxamide-3-nitro-5-α-androst-2-ene.

* * * * *